United States Patent [19]

Torichigai et al.

[11] Patent Number: 4,800,927
[45] Date of Patent: Jan. 31, 1989

[54] CABLE INSERTION NOZZLE

[75] Inventors: Masaaki Torichigai; Keiichi Iwamoto, both of Nagasaki, Japan

[73] Assignee: Mitsubishi Jukogyo Kabushiki Kaisha, Tokyo, Japan

[21] Appl. No.: 919,681

[22] Filed: Oct. 16, 1986

[30] Foreign Application Priority Data

Oct. 23, 1985 [JP] Japan .................... 60-162443[U]

[51] Int. Cl.4 ............................................ F16L 35/00
[52] U.S. Cl. .................................. 138/109; 138/178; 285/261
[58] Field of Search ............... 138/109, 97; 165/76, 165/11.1, 11.2; 464/7, 8; 285/261, 270, 18

[56] References Cited

U.S. PATENT DOCUMENTS

| | | | |
|---|---|---|---|
| 3,962,767 | 6/1976 | Byerley et al. | 138/97 |
| 4,045,054 | 8/1977 | Arnold | 285/261 |
| 4,114,654 | 9/1978 | Richardson | 165/76 |

FOREIGN PATENT DOCUMENTS

| | | | |
|---|---|---|---|
| 0465317 | 12/1952 | Italy | 285/265 |
| 52-28758 | 3/1977 | Japan | 138/97 |

*Primary Examiner*—James E. Bryant, III
*Attorney, Agent, or Firm*—Wenderoth, Lind & Ponack

[57] ABSTRACT

A cable insertion nozzle is provided of the type having a spherical seat formed by two female and male portions of a ball and socket joint, which is characterized in that in the inner peripheral surfaces of the female and male portions is formed a recess which has a rectangular shape in longitudinal cross section and a circular shape in transverse cross section when the axis of the female segment coincides with that of the male segment, and in the recess is floatably inserted a cylindrical member the end portions of which are provided with a collar section and whose inside diameter is substantially identical with the original inside diameter of the female and male segments, whereby no step is created in the inner face of the nozzle, thereby permitting smooth conveying of the cable and the like.

3 Claims, 2 Drawing Sheets

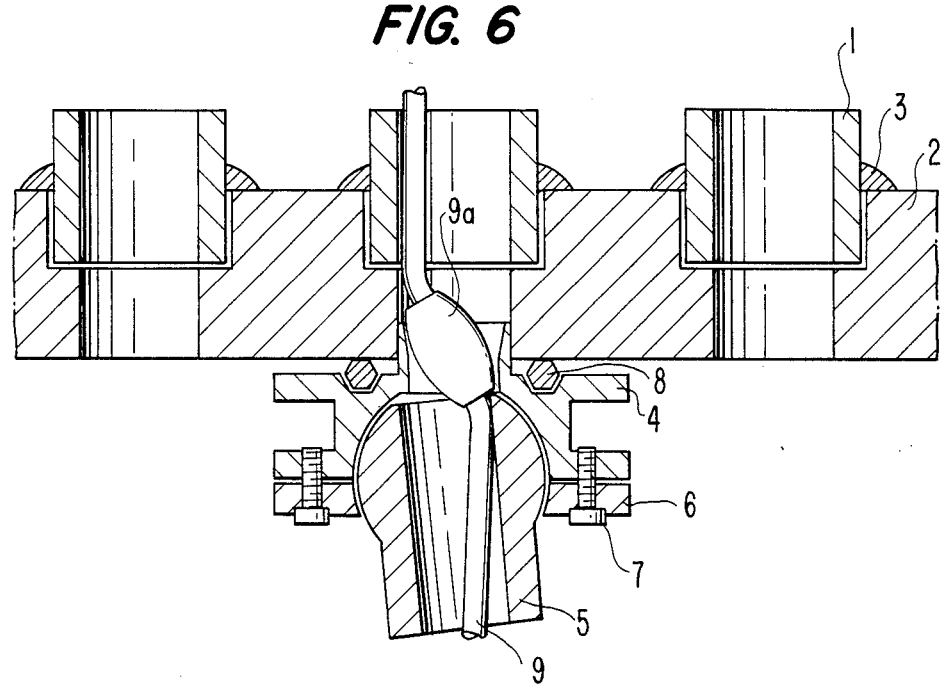
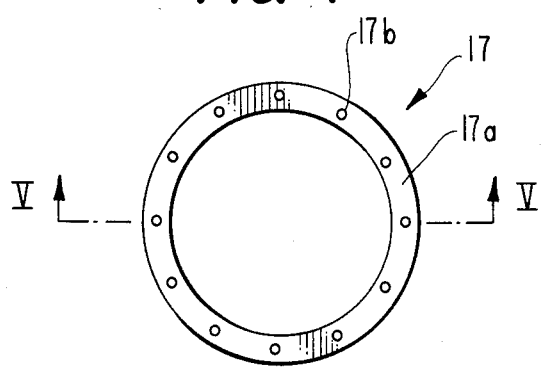
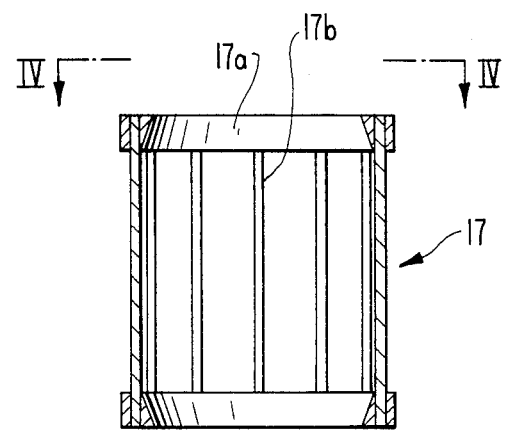

4,800,927

CABLE INSERTION NOZZLE

BACKGROUND OF THE INVENTION

1. Field of the Invention

This invention relates to a nozzle of a manipulator used to insert a cable with a sensor into various heat exchanger pipes in nondestructive inspection of these pipes.

2. Description of Prior Art

Nondestructive inspection of heat exchanger pipes provided in the thermal and nuclear power plants is generally performed by the use of either the ultrasonic flaw detection method or the eddy current examination method, and in either method, a cable with a float, having a sensor at its point, is inserted into the heat exchanger pipes from their respective ends with the aid of pressurized water or compressed air to perform inspection.

FIG. 6 shows the state in which a cable with a float having been inserted in one heat exchanger pipe is going to be withdrawn through a nozzle of a manipulator press-attached to one pipe end section of the heat exchanger pipe (or to a tubesheet) by application of a back pressure. Of course, a nozzle similar to the above is press-attached to the other pipe end section opposite to that shown in FIG. 6 to apply the back pressure thereto. One conventional configuration will now be described with reference to FIG. 6. In FIG. 6, after heat exchanger pipes 1 are inserted in the counterbore section of a tubesheet 2, they are seal-welded as indicated by reference numeral 3. The nozzle section of the manipulator is a ball and socket joint split into a female segment 4 and a male segment 5, these segments are joined together by the use of a nozzle cap 6 and cap screws 7, and a rubber packing 8 is bonded to the sheet face of the female segment 4 to prevent leakage of pressurized water or compressed air. To a cable 9 is attached a float 9a for generating thrust which is effective in conveying (inserting and withdrawing) the cable. In short, the feature of the conventional nozzle is that it is split into two segments and a spherical seat is provided. By the configuration as above, it is easy to insert the nozzle in the pipe end section (hole section) even when the center of the nozzle is dislocated owing to flexure of the manipulator and the like.

However, the spherical seat shown in FIG. 6 tends to create a step at a portion of the spherical seat (in the inner face of the nozzle). Hence, the float 9a is sometimes caught in the course of conveying (inserting and withdrawing) the cable and conveying of the cable becomes unattainable.

SUMMARY OF THE INVENTION

It is an object of the present invention to provide a cable insertion nozzle which does not create a step in the inner face of the nozzle, thereby making conveying of the cable and its float smooth.

To achieve the foregoing object, the present invention provides a cable insertion nozzle of the type having a ball and socket joint with female and male, segments, which is characterized in that in the inner peripheral surfaces of the female and male segments is formed a recess which has nearly a rectangular shape in longitudinal cross section and a circular or substantially circular shape in transverse cross section when the axis of the female segment coincides with that of the male segment, and in the recess is floatably inserted either a cylindrical member or a cage-like member each end portion of which is provided with a collar section and whose inside diameter is substantially identical with the original inside diameter of the female and male segments.

As will be apparent from the foregoing configuration, the nozzle of the present invention does not lose the essential function of the ball and socket joint because a spacing is left between either the cylindrical member or the cage-like member newly inserted in accordance with the present invention and the inner peripheral surface of the joint. Further, since the inside diameter of the cylindrical member or the cage-like member is set equal to that of the female segment and the male segment of the nozzle, no step is created in the inner face of the nozzle, thereby permitting smooth conveying of the cable and float.

BRIEF DESCRIPTION OF THE DRAWINGS

FIGS. 2 and 3 show a cylindrical member to be inserted in a recess formed inside the cable insertion nozzle of the present invention, in which FIG. 2 is a plan view taken in the direction of the arrows along the line II—II of FIG. 3 and FIG. 3 is a longitudinal sectional side view taken in the direction of the arrows along the line III—III of FIG. 2;

FIGS. 4 and 5 show a cage-like member to be inserted in the recess formed inside the cable insertion nozzle of the present invention, in which FIG. 4 is a plan view taken in the direction of the arrows along the line IV—IV of FIG. 5 and FIG. 5 is a longitudinal sectional side view taken in the direction of the arrows along the line V—V of FIG. 4; and FIG. 6 is a longitudinal sectional side view of a cable insertion nozzle of the prior art.

DESCRIPTION OF THE PREFERRED EMBODIMENTS

Embodiments of a cable insertion nozzle according to the present invention will now be described with reference to FIGS. 1 through 5.

Figure 1:
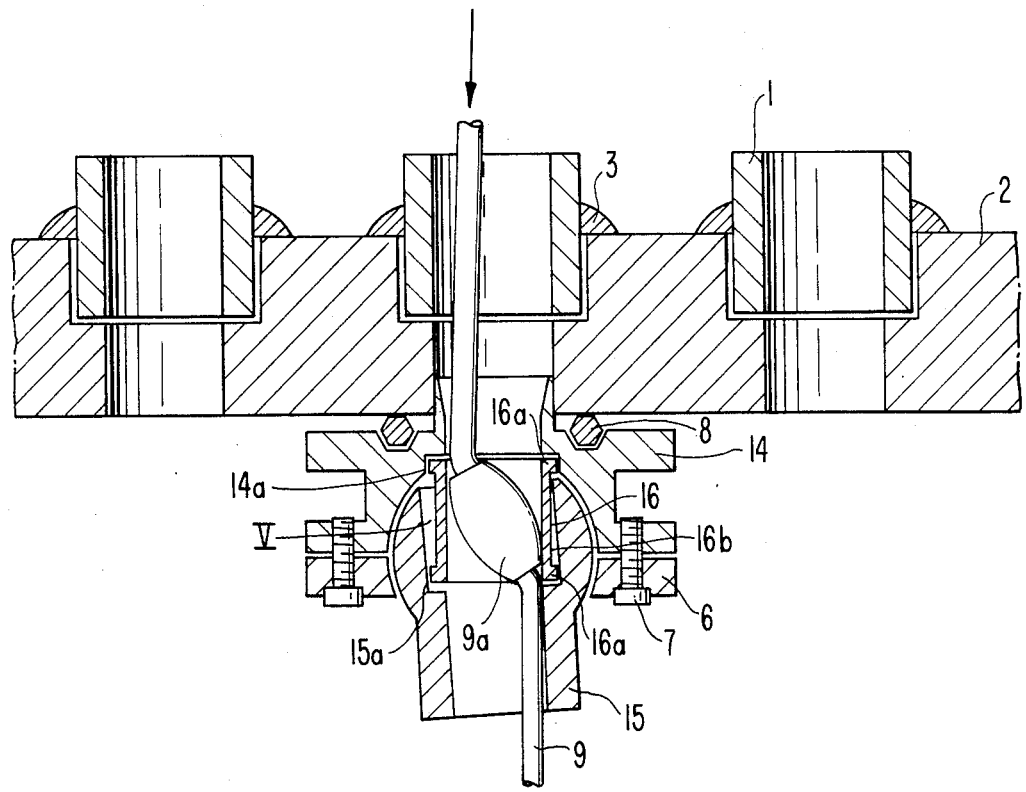
FIG. 1 is a longitudinal sectional side view of a cable insertion nozzle of the present invention in its operating position.

In FIG. 1, members bearing the same reference numerals as in FIG. 6 achieve the same function, and hence, a description thereof is not repeated here.

According to the present invention, in the portion of a ball and socket joint of a cable insertion nozzle joined integrally, i.e. in the inner peripheral surfaces of internal passages through a female segment 14 and a male segment 15, is formed a recess V composed of portions 14a and 15a in segments 14 and 15, respectively; which recess is rectangular in longitudinal cross section and circular in transverse cross section when the longitudinal axes of the female segment 14 and the male segment 15 coincide with each other. In this recess V is floatably inserted a cylindrical member both end portions of which have a radially outwardly projecting collar section 16a thereon having an outer diameter a little smaller than the inside diameter of the recess V and whose inside diameter is substantially identical with the original inside diameter of the female segment 14 and male segment 15, i.e. the inside diameter before the recess is provided. Since the outer peripheral surface of the cylindrical member 16 other than the collar sections 16a, i.e. of its cylinder section 16b, is concave relative to the collar sections so as to form a concavity and creates a V-shaped space in longitudinal cross section between it and the recess portion 15a of the male segment 15, the upper portion of the male segment 15 can oscillate freely within the spherical seat of the nozzle. Further, since the inside diameter of the cylindrical member 16 is made substantially identical with the original inside diameter of the female segment 14 and male segment 15 of the nozzle, no step is created in the inner peripheral surface of the nozzle, so that the cable 9 and the float 9a can be conveyed smoothly.

In addition, if the whole or the inner peripheral surface of the cylindrical member 16 is made of fluorine containing resins such as Teflon (the trade name of polytetrafluoroethylene), conveying of the cable 9 and float 9a can be performed more smoothly because that material has a small frictional resistance.

FIGS. 4 and 5 show a cylindrical member 17 to be inserted in the cutout void formed inside the cable insertion nozzle of the present invention in place of the cylindrical member 16.

Figure 2:
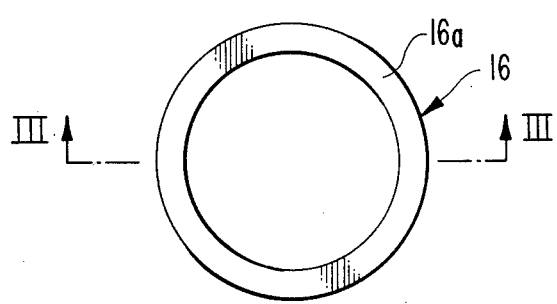
Figure 3:
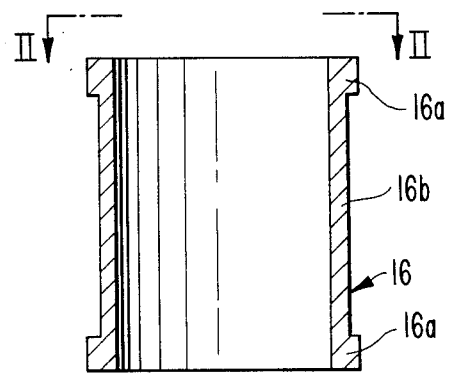

In FIGS. 4 and 5, reference numeral 17a designates rings disposed at the upper and lower end portions, which correspond to the collar sections 16a of the cylindrical member 16 shown in FIGS. 2 and 3. Reference numeral 17b designates piano wires whose upper and lower portions are inserted into holes bored at equal intervals in the circumferential direction of the upper and lower rings 17a and secured there by solder, these wires corresponding to the cylinder section 16b of the cylindrical member 16 shown in FIGS. 2 and 3. Although the cage-like member 17 is made up of the rings 17a and the piano wires 17b, it is identical in function and effect with the cylindrical member 16.

As described hereinabove, the cable insertion nozzle according to the present invention is of the type having a ball and socket joint with female and male, segments, which is characterized in that in the inner peripheral surfaces of the female and male segments is formed the recess which has a rectangular shape in longitudinal cross section and a circular shape in transverse cross section when the axis of the female segment concides with that of the male segment, and in the recess is floatably inserted either the cylindrical member or the cage-like cylindrical member the end portions of which are provided with the collar section and whose inside diameter is substantially identical with the original inside diameter of the female and male segments; thus, the nozzle, or the upper portion of the male segment, can oscillate freely within the spherical seat, and because no step is created in the inner peripheral surface of the nozzle the cable with the float for nondestructive inspection can effectively be inserted and withdrawn easily.

What is claimed is:

1. A cable insertion nozzle comprising:
   a ball and socket joint having male and female portions, which are rotatable relative to each other, and an internal passage therethrough extending along the longitudinal axes thereof and having an original inside diameter, the inner peripheral surfaces of the internal passage in the female and male portions having recesses therein which define a cavity therebetween with the longitudinal axis of the female segment coinciding with the longitudinal axis of the male segment, which cavity has a rectangular shape in longitudinal cross-section and a circular shape in transverse cross-section; and
   a hollow cylindrical member having an interior with an inside diameter substantially the same as the original inside diameter of the internal passages of said male and female portions and positioned in said cavity, said cylindrical member having opposite end portions and a radially outwardly projecting collar on each end portion defining a concavity along the exterior of said cylindrical member, the end of said male portion being opposed to said concavity, so that, said male portion can move into said concavity while the interior of said cylindrical member remains aligned with the internal passage in said female portion and the formation of a step between the female portion and the male portion is avoided.

2. A cable insertion nozzle according to claim 1 wherein the cylindrical member is a cage-like member made up of two end rings and a plurality of piano wires coupled at each end with the respective rings.

3. A cable insertion nozzle according to claim 1, wherein at least the inner peripheral surface of the cylindrical member is made of fluorine containing resins.